United States Patent
Guillon et al.

(10) Patent No.: US 8,058,494 B2
(45) Date of Patent: Nov. 15, 2011

(54) PROCESS FOR THE PRODUCTION OF PHENYLALKANES THAT USES AT LEAST TWO ALKYLATION REACTORS IN PARALLEL

(75) Inventors: Emmanuelle Guillon, Vernaison (FR); Eric Sanchez, Saint Genis Laval (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 897 days.

(21) Appl. No.: 11/664,713

(22) PCT Filed: Oct. 4, 2005

(86) PCT No.: PCT/FR2005/002431
§ 371 (c)(1), (2), (4) Date: Apr. 1, 2008

(87) PCT Pub. No.: WO2006/037885
PCT Pub. Date: Apr. 13, 2006

(65) Prior Publication Data
US 2009/0062583 A1    Mar. 5, 2009

(30) Foreign Application Priority Data

Oct. 6, 2004 (FR) .................................. 04 10557
Nov. 5, 2004 (FR) .................................. 04 11858

(51) Int. Cl.
*C07C 2/66* (2006.01)

(52) U.S. Cl. ......... 585/455; 585/449; 585/467; 585/301

(58) Field of Classification Search ................ 585/455, 585/449, 467, 301
See application file for complete search history.

(56) References Cited

U.S. PATENT DOCUMENTS

| | | | |
|---|---|---|---|
| 5,012,021 A | 4/1991 | Vora et al. | |
| 6,069,285 A | 5/2000 | Fritsch et al. | |
| 6,133,492 A * | 10/2000 | Anantaneni | 585/456 |
| 6,222,084 B1 | 4/2001 | Ghosh et al. | |
| 6,740,789 B1 | 5/2004 | Bozzano et al. | |
| 2004/0138511 A1 | 7/2004 | Butler et al. | |

FOREIGN PATENT DOCUMENTS

EP    1 043 296 A2    10/2000

* cited by examiner

*Primary Examiner* — Thuan Dinh Dang
(74) *Attorney, Agent, or Firm* — Millen, White, Zelano & Branigan, P.C.

(57) ABSTRACT

A process for the production of phenylalkanes comprising at least two catalytic alkylation reactors placed in parallel among which are present in reaction zones that each contain at least one acidic solid catalyst, whereby n is greater than or equal to 2, is described. One of the reactors carries out the alkylation of at least one aromatic compound by at least one olefin that has 9 to 16 atoms. An olefin fraction is introduced at the inlet of each of the reaction zones of the reactor that operates in alkylation mode. While one of the reactors carries out the alkylation, the other reactor carries out the reactivation of each catalyst, partially deactivated, that it contains. The functions of each reactor are switched regularly so as to limit the deactivation of catalysts in each of the reactors.
The phenylalkanes that are obtained by the process according to the invention are particularly suitable for the production of detergents.

24 Claims, 1 Drawing Sheet

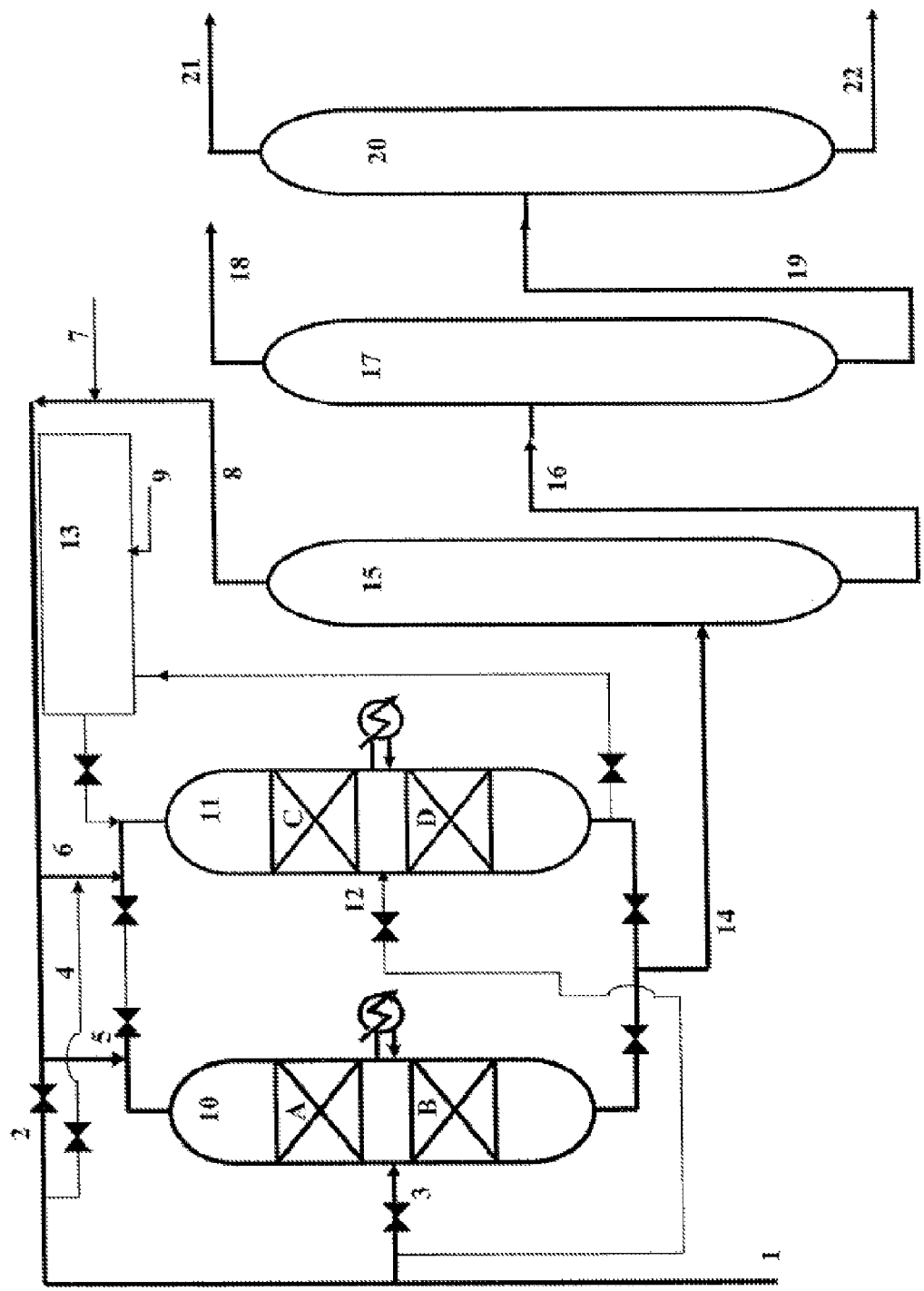

PROCESS FOR THE PRODUCTION OF PHENYLALKANES THAT USES AT LEAST TWO ALKYLATION REACTORS IN PARALLEL

TECHNICAL FIELD

This invention relates to a process for the production of phenylalkanes by alkylation of at least one aromatic compound by means of olefinic hydrocarbons that in general comprise 9 to 16 carbon atoms per molecule.

The phenylalkanes that are obtained according to the process of the invention constitute precursors of choice for the formulation of detergents and in particular certain biodegradable detergents, for example after sulfonation.

PRIOR ART

Currently, the bases for biodegradable detergents rely greatly on alkylbenzenes or phenylalkanes. The production of this type of compound is growing steadily. One of the main properties desired for these compounds, after a sulfonation stage, is, in addition to their detergent power, their biodegradability, which requires that these products be linear alkylbenzenes (LAB) or slightly branched alkylbenzenes (MAB) according to the definition of U.S. Pat. No. 6,187,981.

The alkylbenzenes that are designated above are generally obtained by alkylation of the benzene by means of olefin(s), generally having 9 to 16 carbon atoms.

In general, for obtaining linear alkylbenzenes, the olefinic feedstock that is used contains linear olefins for the most part. By contrast, for obtaining slightly branched alkylbenzenes (MAB), the olefins are branched. For example, U.S. Pat. Nos. 6,670,516 and 6,187,981 describe processes for alkylation of benzene for which the linear olefinic feedstock is modified upstream from the alkylation so as to isomerize the olefins. It seems possible according to U.S. Pat. No. 5,245,094, however, to modify the linearity of the alkylbenzenes that are formed by increasing the temperature of the reaction.

The most known alkylation processes use, during the stage for alkylation of the benzene, the hydrofluoric acid as acid catalyst. This process leads to the formation of the 2-, 3-, 4-, 5- and 6-phenylalkane isomers. The main drawback of this process is linked to environmental constraints and poses severe safety problems, on the one hand, and waste removal problems, on the other hand. In addition, the separation of the catalyst from products of the reaction is necessary and difficult to implement. To resolve these drawbacks, it was proposed to initiate the alkylation of the benzene by linear olefins in the presence of an acidic solid catalyst. The prior art notes the use of numerous acidic solid catalysts for the synthesis of phenylalkanes. Said catalysts can consist of zeolitic compounds as defined in the classification "Atlas of Zeolite Framework Types," W. M. Meier, D. H. Olson and Ch. Baerlocher, 5$^{th}$ Revised Edition, 2001, Elsevier, to which this application also refers. Thus, U.S. Pat. No. 4,301,317 proposes a series of zeolites among which are cancrinite, gmelinite, mordenite, offretite and ZSM-12. Patent Application FR-A-2 697 246 teaches the use of catalysts based on dealuminified Y zeolite. Patent EP-B-160 144 discloses the use of Y zeolites whose crystallinity varies from 30 to 80% while U.S. Pat. No. 5,036,033 teaches the use of Y zeolites that are rich in ammonium cations. Amorphous catalysts such as the silica-aluminas (U.S. Pat. Nos. 4,870,222, 5,344,997, 5,245,094), catalysts based on supported heteropolyanions (FR-A-2,828,486) or clays (U.S. Pat. No. 5,733,439, EP-A-0,711,600) can also be used.

The acidic solid catalysts constitute an advantageous alternative to the use of prior acid catalysts. However, the primary drawback of the acidic solid catalysts is their rapid deactivation during the alkylation reaction by adsorption on the surface and on the active sites of said catalysts of hydrocarbon-containing radicals.

Several patents have already taught solutions for the purpose of limiting and even preventing the deactivation of acidic solid catalysts for alkylation. For example, U.S. Pat. No. 2,541,044 discloses a continuous alkylation process with several reactors in parallel with periodic interruption of the alkylating hydrocarbon so as to allow high-temperature rejuvenation by a stream of alkylated hydrocarbon. In a similar manner, U.S. Pat. No. 5,648,579 discloses a continuous alkylation process in the presence of an acidic solid catalyst whose deactivation is prevented by alternately initiating an alkylation reaction stage (benzene+olefins) and a stage for washing with benzene during which the olefin stream is interrupted for a cycle duration of 10 minutes to 1 hour. Patent U.S. Pat. No. 5,453,553 discloses a process for the production of linear alkylbenzenes in the presence of hydrogen with use of a solid catalyst that comprises a metallic phase in close contact with a zeolite. These prior processes disclosed in U.S. Pat. Nos. 5,648,579 and 5,453,553 dispense with initiating the regeneration of the acidic solid catalyst or make it possible at least to keep the catalyst active over a long period (1 month). The process for alkylation of aromatic hydrocarbons that is disclosed in Patent EP-B1-0 353 813 comprises a periodic regeneration of the acidic solid catalyst with paraffin streams that alternate with alcohol streams for a duration that can reach 8 hours, whereby the cycle duration of the alkylation reaction is on the order of 12 hours. However, these patents teach the use of reactivation elements that increase the use of the processes or mention cycle durations that are not very compatible with an industrial operation.

It is also possible to delay the deactivation of the solid catalyst by an increase of the temperature of the alkylation reaction; however, if the service life of the catalyst is extended, the catalytic selectivity is modified by this type of performance of the process.

It was also considered in Patent U.S. Pat. No. 6,069,285 to eliminate the compounds that are precursors of the deactivation of the alkylation catalyst, in particular aromatic compounds, upstream from the alkylation unit, so that the cycle durations in the alkylation reactor are compatible with an industrial mode of operation. This elimination of the aromatic compounds upstream from the alkylation unit is carried out in a unit that is provided for this purpose that adds weight to the installation of the production chain of the alkylbenzenes.

Also, one of the objects of this invention is to provide a process for the production of phenylalkanes using at least one catalytic reactor that operates in alkylation mode in which the deactivation of each of the acidic solid catalysts present there is delayed so as to allow cycle durations of an alkylation reaction that is extended relative to those of prior processes. Another object of this invention is to provide a process for the production of phenylalkanes whose selectivity in linear products and in a more general way the 2-phenylalkane isomer concentration can be monitored by the control of the process.

SUMMARY AND THE ADVANTAGE OF THE INVENTION

The object of this invention is a process for the production of phenylalkanes that comprises at least:

a) A reaction for alkylation of at least one aromatic compound by at least one olefin that has 9 to 16 carbon atoms per molecule, whereby said reaction is carried out in at least a first catalytic alkylation reactor within which n reaction zones that each contain at least one acidic solid catalyst are present, whereby n is greater than or equal to 2, and at the inlet of each of which at least one fraction of the total amount of olefins necessary to said reaction is introduced, b) The separation of at least a portion of the effluent that is obtained from stage a) to recover the excess reagents, on the one hand, and the phenylalkanes, on the other hand, c) The reactivation of each acidic solid catalyst that is present in each of n reaction zones of at least a second catalytic alkylation reactor that is placed in parallel relative to said reactor(s) used in said stage a), whereby n is greater than or equal to 2, and d) The periodic switching of functions carried out by at least said first catalytic alkylation reactor used in stage a) and at least said second catalytic alkylation reactor that is used in stage c) such that at least said first reactor that is initially used in said stage a) is used under the conditions of said stage c) at the end of a duration that is at least equal to 5 hours and that at least said second reactor that is initially used in said stage c) is used under the conditions of said stage a). The olefins that are used as an alkylating agent in the catalytic alkylation reactor(s) operating in alkylation mode to produce phenylalkanes preferably contain 10 to 14 carbon atoms per molecule. The olefins are preferably for the most part linear. The aromatic compound that is used as a reagent in the catalytic alkylation reactor(s) operating in alkylation mode is preferably benzene.

In a preferred mode of the invention, each of the reaction zones of each of the catalytic alkylation reactors contains at least the same acidic solid catalyst, preferably a zeolitic catalyst. It may also be advantageous to use the same first acidic solid catalyst in each of the reaction zones of at least said first catalytic reactor and the same second acidic solid catalyst in each of the reaction zones of at least said second catalytic reactor, whereby said first acidic solid catalyst is different from said second acidic solid catalyst.

The reactivation according to stage c) of each acidic solid catalyst can be carried out either by rejuvenation or by regeneration or by rejuvenation and regeneration. The regeneration is carried out by combustion of the coke that is formed by the adsorption of a large amount of hydrocarbon-containing radicals on the surface and on the active sites of each of the catalysts.

In a surprising and unexpected way, the applicant discovered that the process according to the invention makes it possible to limit the deactivation of each of the acidic solid catalysts. Thus, the cycle duration of the alkylation reaction is considerably lengthened and the stages for regeneration by combustion of each of the deactivated catalysts are not very frequent. For optimal use of the process according to the invention, the duration of the alkylation reaction in the catalytic reactor(s) operating in alkylation mode is such that the conversion of olefins in the catalytic reactor(s) is maintained or close to 100%, the reactivations by rejuvenation are then optimized, and the total number of reactivation by regeneration is limited. The process according to the invention also has the advantage of producing phenylalkanes whose selectivity in linear products, i.e., not having branches on the alkyl chain carried by the benzene group, can be monitored, which is advantageous because the specifications of desired products, in terms of isomer content, for example 2-phenyl isomer, of dialkylbenzene content, of product linearity, for an application in the formulation of the detergents, are very variable. In addition, the process according to the invention makes it possible, by a careful arrangement of different catalysts, to adjust the selectivity of desired isomer. Another advantage of the invention is the optimization of the amount of aromatic compound(s), preferably benzene, to be introduced into the catalytic reactor(s) operating in alkylation mode. Unlike the prior processes in which the entire amount of olefins is generally introduced at one time, the process according to the invention makes it possible to reduce the amount of benzene that is necessary relative to the prior processes while maintaining the same ratio of aromatic compound(s)/olefins, preferably benzene/olefins, in the catalytic reactor. This invention therefore makes it possible, for example by way of illustration, to double this ratio, and one skilled in the art will easily be able to extend this reasoning to an even more considerable increase of the ratio of aromatic compound(s)/olefins, preferably benzene/olefins, with the same overall flow rate of aromatic compound, preferably benzene (saving of benzene) relative to the prior art. This implementation allows an economy on the level of the initial investment, the operating cost and a cycle duration that is considerably improved relative to the prior art.

DESCRIPTION

The object of this invention is a process for the production of phenylalkanes comprising at least:

a) A reaction for alkylation of at least one aromatic compound by at least one olefin that has 9 to 16 carbon atoms per molecule, whereby said reaction is carried out in at least a first catalytic alkylation reactor within which are present n reaction zones that each contain at least one acidic solid catalyst, whereby n is greater than or equal to 2, and at the inlet of each of which at least one fraction of the entire amount of olefins necessary to said reaction is introduced, b) The separation of at least a portion of the effluent that is obtained from stage a) for recovering the excess reagents, on the one hand, and the phenylalkanes, on the other hand, c) The reactivation of each acidic solid catalyst that is present in each of n reaction zones of at least a second catalytic alkylation reactor that is placed in parallel relative to said reactor(s) used in said stage a), whereby n is greater than or equal to 2, and d) The periodic switching of the functions carried out by at least said first catalytic alkylation reactor used in stage a) and at least said second catalytic alkylation reactor used in stage c), such that at least said first reactor that is initially used in said stage a) is used under the conditions of said stage c) at the end of a duration that is at least equal to 5 hours and such that at least said second reactor that is initially used in said stage c) is used under the conditions of said stage a). The installation that makes it possible to carry out the process for the production of phenylalkanes according to the invention comprises at least two catalytic alkylation reactors in parallel: one operates in alkylation mode and the other operates simultaneously in reactivation mode. It advantageously comprises a first catalytic block that comprises several alkylation reactors placed in series and operates simultaneously in alkylation mode and a second catalytic block that comprises several alkylation reactors that are also placed in series and that operate simultaneously in reactivation mode, whereby the first catalytic block and the second catalytic block are placed in parallel and each operate simultaneously.

In at least each of the first and second catalytic alkylation reactors used in stages a) and c) of the process according to the invention, n reaction zones that each contain at least one acidic solid catalyst, n being greater than or equal to 2, are present. Preferably, n is less than 10. Even more preferably, n is less than or equal to 5. Advantageously, at least said first catalytic alkylation reactor and at least said second catalytic alkylation reactor have the same number n of reaction zones.

According to stage a) of the process according to the invention, there is introduced, at the inlet of each of said reaction zones of at least said first catalytic alkylation reactor, at least one fraction of the total amount of olefins necessary to the alkylation reaction of at least one aromatic compound, preferably benzene, with the $C_9$-$C_{16}$, preferably $C_{10}$-$C_{14}$, olefin(s). The inlet of each of the reaction zones is determined by the level of introduction of each of the olefin fractions. The introduction of each of the olefin fractions can be done, for example, by lateral injection into the reactor in a zone that is located between two successive reaction zones.

Each olefin fraction is generally contained in a hydrocarbon-containing feedstock; the content by weight of olefins generally represents 5 to 100% by weight of said hydrocarbon-containing feedstock that is introduced at the inlet of each of the n reaction zones of at least said first catalytic alkylation reactor. The hydrocarbon-containing feedstock can consist entirely of olefins. It is also advantageous to use, as a hydrocarbon-containing feedstock, an effluent that is obtained from a paraffin dehydrogenation unit placed upstream from the alkylation reactors used in the process according to the invention. In such a case, the hydrocarbon-containing feedstock contains, in addition to olefins, unconverted paraffins in said dehydrogenation unit. The paraffins that are contained in said feedstock are $C_9$-$C_{16}$, preferably $C_{10}$-$C_{14}$, paraffins.

According to stage a) of the process according to the invention, there is introduced—at the inlet of the first reaction zone of at least said first catalytic alkylation reactor—at least a portion, preferably all, of the aromatic compound that is to be alkylated, and a hydrocarbon-containing feedstock that contains a first fraction of at least one olefin that comprises 9 to 16 carbon atoms per molecule, preferably 10 to 14 carbon atoms per molecule, whereby the feedstock can contain paraffins, in particular $C_9$-$C_{16}$, preferably $C_{10}$-$C_{14}$, paraffins and optionally aromatic compounds. Said aromatic compound that is used in stage a) is preferably benzene. A second fraction of said $C_9$-$C_{16}$, preferably $C_{10}$-$C_{14}$, olefin(s) is then introduced at the inlet of the second reaction zone of said first catalytic alkylation reactor where it is mixed with at least a portion of the effluents that are obtained from the first reaction zone. For a catalytic alkylation reactor that has n reaction zones, an nth fraction of said olefin(s) is introduced at the inlet of the nth reaction zone of said first catalytic reactor where it is mixed with at least a portion of the effluents that are obtained from the (n−1)th reaction zone. Preferably, the amount of olefin(s) contained in each of the fractions introduced at the inlet of each of the reaction zones is such that essentially all of said olefin(s) is consumed in the reaction zone where the olefin fraction was introduced. According to stage a) of the process according to the invention, there is introduced, at the inlet of at least one reaction zone, an olefin fraction in an amount such that the ratio of aromatic compound(s)/olefins is between 21 and 200, preferably between 25 and 150, very preferably between 30 and 100, and even more preferably between 50 and 100 in said reaction zone. The amount of olefins contained in each of the fractions introduced into each of the reaction zones can vary according to the reaction zones.

According to a preferred embodiment of the invention, the olefin fraction that is introduced at the inlet of each of said reaction zones of at least said first catalytic reactor that is used in stage a) is such that the ratio of aromatic compound(s)/olefins in each of said reaction zones is between 21 and 200, preferably between 25 and 150, very preferably between 30 and 100, and even more preferably between 50 and 100. Advantageously, the olefin fraction that is introduced at the inlet of each of said reaction zones is such that the ratio of aromatic compound(s)/olefins is close (except for the consumption of benzene) in each of said reaction zones. One skilled in the art will then adjust the amount of olefins in each of the olefin fractions introduced into each of the reaction zones. It is also very advantageous that the olefin fraction introduced into each of said reaction zones represents 1/n of the total amount of olefins necessary to the alkylation reaction, where n represents the number of reaction zones and n≧2. For example, for a catalytic reactor that has 3 reaction zones, it is advantageous that one third of the total amount of olefins necessary to the alkylation reaction is introduced at the inlet of the first reaction zone, that a second third is introduced at the inlet of the second reaction zone, and that the third third is introduced at the inlet of the third reaction zone. In the expression "ratio of aromatic compound(s)/olefins," it is necessary to include by aromatic compound(s) the aromatic compound(s) introduced exclusively at the inlet of the first reaction zone.

The operating conditions applied within at least said first catalytic alkylation reactor used in stage a) of the process according to the invention are selected by one skilled in the art, in particular based on the nature and the composition of each of the acidic solid catalysts and the specification of the desired product. Advantageously, each of the reaction zones is operated at a temperature that is less than 400° C., preferably between 50 and 350° C., very preferably between 70 and 300° C., and even more preferably between 80 and 250° C., and under a pressure of 1 to 10 MPa, preferably from 1 to 7 MPa with a liquid hydrocarbon flow rate (volumetric flow rate) of about 0.01 to 80, preferably 0.05 to 30, volumes per volume of catalyst and per hour.

The alkylation reaction used in at least said first catalytic alkylation reactor used for carrying out stage a) of the process according to the invention is followed by at least one stage for separation b) of at least a portion, preferably all, of the effluent that is obtained from stage a) so as to recover at least the excess reagents, on the one hand, i.e., the aromatic compound(s), preferably benzene, and the olefins and the phenylalkanes, on the other hand. More specifically, at the outlet of at least said first catalytic alkylation reactor used for carrying out stage a) of the process according to the invention, in general the product that is obtained is fractionated so as to collect separately a first effluent that contains at least the aromatic compound, preferably benzene, unconverted, a second effluent that contains at least one $C_9$-$C_{16}$, preferably $C_{10}$-$C_{14}$, olefin, unconverted, as well as paraffins and optionally aromatic compounds that are initially present in the hydrocarbon-containing feedstock, a third effluent that contains 2-, 3-, 4-, 5- and 6-phenylalkanes, and a fourth effluent that contains at least one polyalkylbenzene (or polyalkylbenzene fraction), whereby the latter can optionally be at least partially recycled to at least one of the n reaction zones, preferably to the first reaction zone of the catalytic alkylation reactor that operates in alkylation mode, where it reacts with the aromatic compound, preferably benzene, upon contact of the acidic solid catalyst that is present there, so as to be at least partially transalkylated (transalkylation reaction), and a mixture of 2-, 3-, 4-, 5- and 6-phenylalkanes is collected.

According to the invention, the installation that makes it possible to implement the process according to the invention comprises at least two catalytic alkylation reactors that are placed in parallel relative to one another, one operating in alkylation mode and the other operating in reactivation mode, each of said reactors having n reaction zones that each contain at least one acidic solid catalyst (n≧2). According to stage c) of the process according to the invention, each acidic solid catalyst that is present in each of the n reaction zones of at least said second catalytic alkylation reactor is reactivated so that the initial activity is recovered. The reactivation according to stage c) of each acidic solid catalyst can be carried out either by rejuvenation or by regeneration or else by rejuvenation and regeneration. It makes it possible to eliminate the hydrocarbon-containing radicals that are adsorbed on the active sites of each of the acidic solid catalysts during the prior alkylation reaction, whereby said radicals are responsible for at least partial deactivation of each of the catalysts.

A first reactivation mode is carried out by rejuvenation, which consists in reactivating each of said acidic solid catalysts in the presence of at least one aromatic compound. More specifically, it consists in washing each of said acidic solid catalysts that is at least partially deactivated by at least one aromatic compound that is introduced at the top of the catalytic reactor. Preferably, said aromatic compound is obtained at least in part from the separation stage b). Advantageously, said aromatic compound is benzene. The rejuvenation is carried out in the absence of olefinic hydrocarbons. Each of the reaction zones of at least said second catalytic alkylation reactor each containing at least one acidic solid catalyst that is at least partially deactivated is operated at a temperature that is usually greater than the temperature at which the alkylation reaction is implemented. Preferably, the temperature at which the rejuvenation is carried out is higher than 100° C., more preferably higher than 150° C., and even more preferably higher than 200° C. The rejuvenation is carried out under a total pressure of more than 1 MPa, with a flow rate of aromatic compound(s), preferably of benzene, of about 0.01 to 80, preferably 0.1 to 50, volumes per volume of catalyst and per hour. The rejuvenation is carried out for an adequate duration, advantageously between 10 and 50 hours, preferably between 12 and 24 hours, so as to ensure the complete elimination of hydrocarbons adsorbed on the active sites of each of the acidic solid catalysts.

A second reactivation mode is carried out by regeneration of each of the acidic solid catalysts. The latter is carried out by combustion of the hydrocarbon-containing radicals that are adsorbed on the active sites of said catalysts. The regeneration is carried out when the amount of hydrocarbon-containing radicals adsorbed on the active sites of each of the acidic solid catalysts is large and is such that coke is deposited on the surface of each of said catalysts. More specifically, the regeneration of each of the acidic solid catalysts by combustion comprises a first stage that consists in heating, under a cover gas, to a temperature that is higher than 100° C., preferably between 150 and 250° C., preferably between 200 and 300° C., said deactivated catalysts so as to eliminate the adsorbed liquid hydrocarbons and a second stage that consists in bringing into contact each of the catalysts with a gas that contains oxygen by gradually increasing the temperature until the exothermal combustion reaction of the coke is observed, in general between 300 and 600° C. The first stage makes it possible to avoid any risk of uncontrolled exothermicity during the second stage, which corresponds to the combustion itself of the coke. This combustion is carried out with care, and the operating conditions are adjusted so that preferably the temperature does not exceed 550° C. and very preferably does not exceed 500° C. (managed combustion). The majority of the coke is burned during the combustion stage: the content by weight of residual coke of the catalyst after combustion is generally less than about 20%, preferably less than about 10%, of the coke content of the catalyst before combustion. The gas that contains oxygen that is used during the combustion stage is generally a mixture of oxygen and cover gas, advantageously containing 0.1 to 20% by volume of oxygen, preferably 0.2 to 10% by volume of oxygen. It may be, for example, air or air diluted in a cover gas. The proportion of oxygen in the gas that is used for the combustion of the coke can also be variable based on the development of the exothermal combustion reaction. A reactivation by regeneration generally lasts longer than a reactivation by rejuvenation: preferably, the regeneration is carried out for a duration of between 20 and 100 hours.

A third reactivation mode is carried out by combining both the rejuvenation and the regeneration, whereby the rejuvenation is carried out before the regeneration. The conditions of the rejuvenation and those of the regeneration are identical to those described above for the implementation of the first and second embodiments of the reactivation. This third mode is particularly suitable when the rejuvenation does not make it possible to regain an optimal performance level, in particular in terms of catalytic activity. The regeneration subsequent to the rejuvenation is carried out on a catalyst from which liquid hydrocarbons are virtually removed.

The process according to the invention is a continuous process in which the production of phenylalkanes is not interrupted at any time. The continuous production of phenylalkanes by alkylation of at least one aromatic compound by at least one $C_9$-$C_{16}$ olefin is made possible by periodically carrying out the switching of functions carried out by at least said first and second catalytic alkylation reactors according to stage d) of the process according to the invention. The alkylation reaction carried out in at least said first catalytic alkylation reactor for a duration of at least 5 hours is interrupted so as to reactivate each of the acidic solid catalysts that are present in at least said first catalytic alkylation reactor while simultaneously the alkylation reaction is resumed in at least said second catalytic alkylation reactor by introducing at least a fraction of the total amount of olefins necessary for the reaction at the inlet of each of the n reaction zones of at least said second catalytic alkylation reactor, whereby said alkylation reaction in at least said second catalytic alkylation reactor is subsequent to a reactivation of each of the acidic solid catalysts that are present in each of the n reaction zones of at least said second catalytic alkylation reactor. The alkylation reaction in at least said second catalytic alkylation reactor is carried out by means of reactivated acidic solid catalysts, either by rejuvenation, or by regeneration, or by rejuvenation and regeneration. The periodicity of the switching is such that a catalytic alkylation reactor operates at least five hours in alkylation mode, preferably at least 10 hours and very preferably at least 24 hours. It goes without saying that the deactivation of each acidic solid catalyst is all the greater the longer the reaction duration within a catalytic alkylation reactor is. Consequently, it is advantageous, to avoid initiating a reactivation by regeneration after each reaction in a catalytic alkylation reactor, that the duration of each alkylation reaction not exceed 168 hours. Under these conditions, each acidic solid catalyst is not very deactivated and is easily reactivated by rejuvenation, simpler to implement than the regeneration. It is actually sufficient to interrupt the stream of olefins at the inlet of each of the n reaction zones of the catalytic alkylation reactor containing said deactivated acidic solid catalysts. By thus initiating regular switching between the functions in alkylation and reactivation mode, the conversion into olefins in the catalytic alkylation reactor operating in alkylation mode is maintained at a maximum rate, in general more than 90%, preferably more than 95%, and very preferably equal to 100%. Advantageously, the rejuvenation is carried out on acidic solid catalysts that have an olefin conversion rate that is equal to 100%. A reactivation by regeneration is initiated in a catalytic alkylation reactor when in general several alkylation/rejuvenation cycles have been operated within said catalytic alkylation reactor and the conversion into olefin(s) is less than 100%, generally less.

According to the invention, at least a first catalytic alkylation reactor and at least a second catalytic alkylation reactor, placed in parallel relative to one another, have n reaction zones that each contain at least one acidic solid catalyst. According to a first embodiment of the invention, the same acidic solid catalyst is used in each of the n reaction zones of each of said first and second catalytic alkylation reactors. For example, it may involve a crystallized or amorphous, acidic solid alkylation catalyst. "Same acidic solid catalyst" is defined as a catalyst that has the same chemical nature and the same chemical composition in each of the n zones. For example, when the catalyst is a zeolitic catalyst that contains a zeolite such as those described below, each of the n reaction zones contains a catalyst based on a zeolite of the same structural type and having the same chemical composition, i.e., the same X/T ratio, whereby X is selected from among silicon and germanium, T is selected from among aluminum, iron, gallium, boron, titanium, vanadium, zirconium, molybdenum, arsenic, antimony, chromium and manganese.

The same acidic solid catalyst that is present in each of the n reaction zones of at least said first and second catalytic alkylation reactors advantageously comprises at least one zeolite of crystalline structure, for example having a structure as defined in the classification "Atlas of Zeolite Framework Type," (W. M. Meier, D. H. Olson and Ch. Baerlocher, $5^{th}$ Revised Edition, 2001, Elsevier). Preferably, the catalyst comprises at least one zeolite that is selected from the group that consists of the zeolites of structural types FAU, MOR, MTW, OFF, MAZ, BEA and EUO. Among the FAU-structural-type zeolites, the Y zeolite and the Y zeolite exchanged with rare earths (REY) are preferred. Among the MOR-structural-type zeolites, the mordenite zeolite is preferred. Among the MTW-structural-type zeolites, the ZSM-12 zeolite is preferred. Among the OFF-structural-type zeolites, the offretite zeolite is preferred. Among the MAZ-structural-type zeolites, the ZSM-4 zeolite is preferred. Among the BEA-structural-type zeolites, the beta zeolite is preferred, and among the EUO-structural-type zeolites, the EU-1 zeolite is preferred.

According to this first embodiment that consists in using the same acidic solid catalyst in each of the n reaction zones of at least said first and second catalytic alkylation reactors that are used for the implementation of the process according to the invention, it is advantageous, when said catalyst is amorphous, to use a catalyst that contains a silica-alumina-type solid.

Preferably, the catalyst that is contained in each of the reaction zones of at least said first and second catalytic alkylation reactors that are used for the implementation of the process according to the invention comprises at least one Y zeolite, advantageously a dealuminified Y zeolite, with an overall Si/Al atomic ratio of more than 4, preferably between 8 and 100, and even more advantageously between 15 and 80. The dealuminified Y zeolite is generally used mixed with at least one binder or a matrix that is generally selected from the group that is formed by clays, aluminas, silica, magnesia, zirconia, titanium oxide, boron oxide and any combination of at least two of these oxides such as silica-alumina, silica-magnesia. All of the known methods for agglomeration and shaping are applicable, such as, for example, extrusion, pelletizing, drop coagulation, etc. The catalyst that is contained in each of the reaction zones of said first and second catalytic alkylation reactors generally contains 1 to 100%, preferably 20 to 98%, very preferably 40 to 98% of said dealuminified Y zeolite, and 0 to 99%, preferably 2 to 80%, and very preferably 2 to 60% by weight of a binder or a matrix. The dealuminified Y zeolites and their preparation are known. Reference can be made to, for example, Patent U.S. Pat. No. 4,738, 940.

The Y zeolite, which may or may not be dealuminified, present in each of the acidic solid catalysts contained in each of the n reaction zones of least said first and second catalytic alkylation reactors, is preferably at least partially in acidic form (HY zeolite) and is characterized by different specifications:

An overall Si/Al atomic ratio that is greater than 4, preferably between 8 and 100, and even more preferably between 15 and 80, A sodium content that is less than 0.25% by weight, A crystalline parameter of the elementary mesh that is less than $24.55 \cdot 10^{-10}$ m, and preferably, between $24.20 \cdot 10^{-10}$ m and $24.39 \cdot 10^{-10}$ m, A specific surface area that is determined by the B.E.T. method of more than about 300 m$^2$/g and preferably more than about 450 m$^2$/g.

The dealuminified Y zeolites are, for example, synthesized, generally from an NaY zeolite, by a suitable combination of two basic treatments: a) a hydrothermal treatment that combines temperature—the temperature preferably being between 450 and 800° C. and very preferably between 550 and 700° C.—and partial water vapor pressure (between 40 and 100% water vapor), and (b) an acid treatment preferably by a strong and concentrated mineral acid (1 to 15 N). Generally, the NaY zeolite, from which the Y zeolite that is used in each of the catalysts that are present in each of the reaction zones of at least a first and at least a second catalytic alkylation reactor is prepared, has an overall Si/Al atomic ratio of between about 1.8 and 3.5; it will first be suitable to lower its content by weight of sodium to less than 3% and, preferably, to less than 2.5%. The reduction of the sodium content can be done by ion exchanges of the NaY zeolite in ammonium salt solutions (nitrate, sulfate, oxalate, etc.) of an ammonium concentration of between 0.01 and 10 N, at a temperature of between 10 and 180° C. (exchange optionally under autogenous pressure), for a duration of more than about 10 minutes. The NaY zeolite also generally has a specific surface area of between about 750 and 950 m$^2$/g.

It is also advantageous to use a mixture of catalysts as an acidic solid catalyst in each of the reaction zones of at least the first and second catalytic alkylation reactors. It may involve, for example, a mixture of a crystallized catalyst and an amorphous catalyst. It may also involve a mixture of zeolites that consist of least one Y zeolite as described above and at least one MOR-structural-type zeolite, in particular a mordenite zeolite.

Involving the preparation of a catalyst that comprises a zeolite mixture, the mixing of said zeolites, which are in the powder state, is carried out by all of the powder-mixing techniques that are known to one skilled in the art and followed by shaping. When the mixing of the zeolite powders is completed, the mixture is shaped by any technique that is known to one skilled in the art. It can be mixed in particular with a matrix, generally amorphous, for example with a wet powder of alumina gel. The shaping can also be done with matrices other than alumina, such as, for example, magnesia, amorphous silica-aluminas, natural clays (kaolin, bentonite, sepiolite, attapulgite), silica, titanium oxide, boron oxide, zirconia, aluminum phosphates, titanium phosphates, zirconium phosphates, carbon and mixtures thereof. It is also advantageously possible to use mixtures of alumina and silica, mixtures of alumina and silica-alumina. It is preferred to use matrices that contain alumina, in all of its forms that are known to one skilled in the art, and even more preferably gamma-alumina. The mixture is then shaped. Several techniques can be used for this purpose and in particular extrusion through a die, pelletizing and tabletting. The mixture of zeolites can also consist of a mixture of already shaped zeolites, as described above. It is also possible to prepare a catalyst that comprises a mixture of zeolites for mixing a first shaped zeolitic catalyst with a second shaped zeolitic catalyst.

The catalyst that is contained in each of the reaction zones of at least the first and the second catalytic alkylation reactors for the implementation of the process according to the invention is shaped in the form of grains with different shapes and sizes. It is used in general in the form of cylindrical or multilobar extrudates, such as bilobar, trilobar or multilobar extrudates of straight or twisted shape, but it can optionally be produced and used in the form of crushed powder, tablets, rings, balls, or disks.

After the shaping stage, the product that is obtained is subjected to a drying stage at a temperature of between 100 and 300° C., preferably between 120 and 200° C., then to a calcination stage at a temperature of between 300 and 600° C., preferably between 350 and 550° C.

The acidic solid catalyst that is contained in each of the reaction zones of at least the first and second catalytic alkylation reactors used for the implementation of the process according to the invention preferably comprises a Y zeolite, a mordenite zeolite or a mixture of zeolites consisting of at least one Y zeolite and at least one mordenite zeolite. The preparation of MOR-structural-type zeolites is known in the prior art (U.S. Pat. No. 4,503,023).

According to a second embodiment of the invention, the same first acidic solid catalyst is used in each of the n reaction zones of at least said first catalytic alkylation reactor, and the same second acidic solid catalyst is used in each of the n reaction zones of at least said second catalytic alkylation reactor. Said first acidic solid catalyst has a different nature and/or chemical composition from that (those) of said second acidic solid catalyst. Said first and second acidic solid catalysts can be amorphous or crystallized. They can also consist of a mixture of catalysts, for example a mixture of an amorphous catalyst and a crystallized catalyst or a mixture of two crystallized catalysts, different from one another by their structural type and/or their chemical composition. Advantageously, said first and second acidic solid catalysts are zeolitic: they comprise at least one zeolite that is selected from the group that consists of the zeolites of structural types FAU, MOR, MTW, OFF, MAZ, BEA and EUO, whereby the zeolite that is present in said first acidic solid catalyst that is contained in each of the n reaction zones of at least said first catalytic alkylation reactor has a structural type and/or a chemical composition of its framework that is different from the zeolite that is present in said second acidic solid catalyst that is contained in each of the n reaction zones of at least said second catalytic alkylation reactor. For example, said first acidic solid catalyst comprises a MOR-type zeolite, preferably a mordenite, and said second acidic solid catalyst comprises an FAU-structural-type zeolite, preferably a Y zeolite and very preferably a dealuminified Y zeolite. It is also very advantageous to use a mixture of a Y zeolite and a mordenite as first or as second solid alkylation catalysts. The characteristics of the Y and mordenite zeolites as well as the preparation of an acidic solid catalyst comprising a mixture of zeolites have already been described above. The advantage of using acidic solid catalysts that differ by their nature and/or their chemical composition in at least each of said first and second catalytic alkylation reactors is the possibility of modulating the selectivity of 2-phenylalkanes of the final product.

According to a third embodiment of the invention, at least two reaction zones of at least said first or said second catalytic alkylation reactor contain a different acidic solid catalyst. For example, a reaction zone contains an acidic solid catalyst that comprises a Y zeolite, preferably a dealuminified Y zeolite, and another reaction zone of the same catalytic alkylation reactor comprises a mordenite zeolite.

The process according to the invention is advantageously used for the production of detergents. It is preferably integrated in a complex chain that is designed for the production of detergents.

The invention will be better understood from reading the following non-limited detailed example of a particular embodiment of a device that allows the implementation of the process according to the invention (FIG. 1).

Fresh benzene that arrives via the pipe 7 is mixed with benzene that comes, via the pipe 8, from the top of a first fractionation column 15 and with a hydrocarbon-containing feedstock that comprises $C_9$-$C_{16}$, preferably $C_{10}$-$C_{14}$, olefins and $C_9$-$C_{16}$, preferably $C_{10}$-$C_{14}$, paraffins, brought by the pipe 2. The amount of olefins present in the feedstock brought through the pipe 2 represents half the total amount of olefins present in the initial hydrocarbon-containing feedstock brought via the pipe 1. The overall mixture that is obtained (benzene and hydrocarbon-containing feedstock with olefins and paraffins), introduced into pipe 5, which may or may not undergo reheating by any means known to one skilled in the art, constitutes the feedstock of the first reaction zone A of the alkylation reactor 10. The alkylation reactor 10 comprises two separate reaction zones A and B, each containing a solid alkylation catalyst.

A second $C_9$-$C_{16}$, preferably $C_{10}$-$C_{14}$, olefin fraction, accompanied by $C_9$-$C_{16}$, preferably $C_{10}$-$C_{14}$, paraffins, is introduced via the pipe 3 directly into the reactor 10, whereby the injection point is located between the two reaction zones A and B or optionally inside the catalytic bed. The supply of the second reaction zone B (after injection of the second olefinic fraction) consists of the reaction effluent that is obtained from the first reaction zone A and the olefinic fraction that is introduced via the pipe 3 mentioned above.

At the outlet of the catalytic alkylation reactor 10, the reaction effluent that consists of the reaction products is sent, after optional cooling, via the pipe 14 to a separation section. This separation section, comprising several fractionation columns or any other means known by one skilled in the art, has as its object to separate the desired reaction products and the unconverted products in the upstream reaction units such as, for example, the unit for dehydrogenation or alkylation (for example, olefin and paraffins). The reaction effluent that is obtained from the reactor 10 and the reactivation effluent obtained from reactor 11 are mixed in the pipe 14 and are separated to constitute the streams recycled to the various units constituting the entire production scheme (for example, the benzene that is recycled at the inlet of a catalytic alkylation reactor and the unconverted paraffins that are recycled at the inlet of a dehydrogenation unit that is placed upstream from the catalytic alkylation reactors when said reactors are integrated in a LAB production chain) and the production streams desired by this invention. For example, if fractionation columns are used as a separation means, the top of the first fractionation column 15 consists of excess benzene that has not reacted and then is recycled via the pipe 8. At the bottom of this first fractionation column 15, a fraction that is sent via the pipe 16 to a second fractionation column 17 is collected. At the top of this second fractionation column 17, for the most part the $C_9$-$C_{16}$, preferably $C_{10}$-$C_{14}$, olefins, non-transformed, as well as the paraffins initially present in the hydrocarbon-containing feedstock, are collected via the pipe 18. At the bottom of this second fractionation column 17, a mixture that is sent via the pipe 19 to a third fractionation column 20 is drawn off. At the top of this third fractionation column 20, for the most part a mixture of 2-phenylalkane, 3-phenylalkane, 4-phenylalkane, 5-phenylalkane and 6-phenylalkane, which is sent into storage via the pipe 21, is collected. At the bottom of this third fractionation column 20, for the most part dialkylbenzenes or other heavy products are drawn off via the pipe 22, and said products can be at least partly recycled to a transalkylation reactor (not shown in the FIGURE) so as to increase the overall yield of the desired product.

The second catalytic alkylation reactor 11, during the operating period in alkylation mode of the reactor 10, operates in reactivation mode. There is then no feedstock comprising $C_9$-$C_{16}$, preferably $C_{10}$-$C_{14}$, olefins, optionally accompanied by $C_9$-$C_{16}$, preferably $C_{10}$-$C_{14}$, paraffins, circulating in the pipes 12 and 4. The reactor 11 that operates, for example, in rejuvenation mode is fed via the pipe 6 with benzene, having undergone reheating, obtained from the top of the first separation column 15. The effluent of the alkylation reactor 11 that operates in reactivation mode by rejuvenation is mixed with the effluent of the alkylation reactor 10 to constitute the supply of the first separation column 15. When the reactivation mode of each catalyst that is contained in, for example, the reactor 11 operates in regeneration mode, no flow passes via the pipe 6, and each acidic solid catalyst that is contained in each of the reaction zones C and D of the reactor 11 is brought into contact with a gaseous mixture that contains primarily the nitrogen and the oxygen introduced via the pipe 9 into the unit 13 that ensures the regeneration loop so as to subject each catalyst to a managed combustion.

At the end of the reactivation period (by rejuvenation and/or regeneration), the alkylation reactor 11 is waiting for switching with the alkylation reactor 10. During the switch, so that the reactor 11 operates in alkylation mode and the reactor 10 operates in reactivation mode, the pipes 2 and 3 are no longer used, and the hydrocarbon-containing feedstock brought via the pipe 1 and that contains at least $C_9$-$C_{16}$, preferably $C_{10}$-$C_{14}$, olefins, accompanied by $C_9$-$C_{16}$, preferably $C_{10}$-$C_{14}$, paraffins, is oriented toward the pipes 12 and 4 so as to be mixed with a benzene stream from the pipe 6.

The following examples are provided by way of illustration of the implementation of the process according to the invention.

EXAMPLE 1

Preparation of Catalyst A Containing a Dealuminified Y Zeolite

An NaY zeolite of formula $NaAlO_2(SiO_2)_{2.5}$ is used as a raw material. This zeolite is subjected to 5 successive exchanges in ammonium nitrate solutions with a 2N concentration, at a temperature of 95° C., for a duration of 2 hours, and with a ratio of solution volume to zeolite weight that is equal to 8 cm³/g. The level of sodium of the $NH_4Y$ zeolite that is obtained is 0.83% by weight. This product is then quickly introduced into a furnace that is preheated to 770° C. and left for 4 hours in a static atmosphere. The zeolite is then subjected to an acid treatment under the following conditions: the ratio between the 3N nitric acid volume and the solid weight is equal to 9 cm³/g, the temperature is 95° C., and the treatment duration is 3 hours. Then, another treatment under the same conditions is carried out, but with a 0.5 N nitric acid solution.

The thus obtained zeolite has a content by weight of sodium of 0.14% and an Si/Al atomic ratio that is equal to 38.

The zeolite is shaped by extrusion with the alumina (50% by weight of zeolite and 50% by weight of alumina). The extrudates are then dried at 120° C. for one night, then calcined at 550° C.

EXAMPLE 2

Preparation of Catalyst B Containing a Mordenite Zeolite

A mordenite zeolite in sodium form, whose chemical formula in the anhydride state is $Na_1AlO_2(SiO_2)_{5.1}$ and its sodium content is 5% by weight, is used. 100 grams of this powder is brought to reflux at 100° C. for 2 hours in a 4N ammonium nitrate solution with a V/P ratio that is equal to 4 cm³/g. This cationic exchange operation is repeated 3 times. The content by weight of sodium of the product that is obtained is about 500 ppm (parts per million).

This product is then subjected to an acid attack using a 4.5 N nitric acid aqueous solution, and the product is brought to reflux in this aqueous solution for 2 hours with a V/P ratio that is equal to 4 cm³/g. After this treatment, the product is washed with demineralized water.

The mordenite that is obtained has an Si/Al atomic ratio that is equal to 40 and a sodium content that is equal to 20 ppm by weight.

The thus obtained mordenite is then mixed with an alumina gel (50% by weight of mordenite and 50% by weight of alumina gel). The mixture that is obtained is shaped in the form of extrudates with a diameter that is equal to about 1.8 mm by passage through a die. The extrudates are then dried in an oven at 120° C. for one night, then calcined in dry air at 550° C.

EXAMPLE 3

Production of Phenylalkanes (According to the Invention)

Two catalytic reactors 1 and 2 in parallel, each comprising two reaction zones that contain 25 cm³ of catalyst A in the form of extrudates, prepared according to Example 1, are used.

The reactor 1 is in alkylation phase. The reactor 2 is in rejuvenation phase.

For the reactor 1, the operating conditions for the alkylation of the benzene for each reaction zone are the following:
Temperature: 120° C.
Pressure: 4 MPa
VVG close to 2 $h^{-1}$ (volume of liquid hydrocarbons per volume of catalyst and per hour)
Molar ratio {benzene/dodecene-1} in each of the reaction zones≈60

A feedstock that contains 86% by weight of benzene and 14% by weight of olefins (C10-C14) is prepared. This feedstock that is introduced at the inlet of the first reaction zone contains all of the benzene that is necessary for the alkylation reaction and half the amount of olefins necessary for the alkylation reaction. The other half, corresponding to an amount of olefins that is identical to that present in the feedstock introduced at the inlet of the first zone, is introduced at the inlet of the second reaction zone by a lateral injection in the middle of the catalytic reactor.

The results that are obtained are presented in Table 1.

TABLE 1

| Cycle Duration with Conversion of Olefins >95% | 36 hours |
|---|---|
| Linearity of the Product Obtained (% by Weight) | 93.2 |
| Composition of the Product (% by Weight) | |
| 2-Phenylalkane | 28.3 |
| 3-Phenylalkane | 23.1 |
| 4-Phenylalkane | 19.9 |
| 5-Phenylalkane | 13.1 |
| 6-Phenylalkane | 12.1 |
| Didodecylbenzene (% by Weight) | 2.8 |
| Heavy Residue (% by Weight) | 0.7 |

The linearity is defined as being equal to the mass ratio [LAB/(LAB+BAB)], whereby the LAB are the linear alkylbenzenes and the BAB are the branched alkylbenzenes, i.e., branched. The 2-phenylalkane, 3-phenylalkane, 4-phenylalkane, 5-phenylalkane, and 6-phenylalkane mixture contains both LAB and BAB.

For the reactor 2, the rejuvenation phase is carried out according to the following operating conditions under a stream of pure benzene:

Temperature: 250° C.
Pressure: 4 MPa
VVH=1.3 h$^{-1}$ (volume of benzene per volume of catalyst and per hour).

The rejuvenation phase in the reactor 2 lasts for about 24 hours (temperature slope included), then each catalyst in each of the reaction zones of the reactor 2 is left for about 12 hours at 120° C. under a stream of benzene until the end of the cycle, in the reactor 1, at the end of which the conversion into olefins is less than 95%. When the conversion into olefins, in the reactor 1, is less than 95%, the functions of each of the reactors are switched: the reactor 1 passes into rejuvenation phase, the reactor 2 into alkylation phase.

After five alkylation/rejuvenation cycles per reactor, the cycle duration during which the conversion of the olefins is greater than 95% decreases. When it becomes equal to 24 hours, a reactivation phase by regeneration of each catalyst in each of the zones (combustion of the coke that is present in each catalyst with an O2/N2 mixture at a temperature that is higher than 450° C.) is initiated alternately in each of the reactors 1 and 2. When each catalyst of each of the reaction zones of reactor 2 is regenerated, the reactor 1 operates in alkylation mode and then vice versa.

EXAMPLE 4

Production of Phenylalkanes (According to the Invention)

Example 3 is used again except for the nature of the acidic solid catalysts that are used. Each of the two reaction zones of each of the reactors 1 and 2 contains a catalyst that consists of a mixture of 50% by weight of catalyst A based on dealuminified Y zeolite and 50% by weight of catalyst B based on mordenite zeolite.

The operating conditions of the alkylation reaction are identical to those used in Example 3. The results that are obtained are presented in Table 2.

TABLE 2

| Cycle Duration with Conversion of Olefins >95% | 39 hours |
|---|---|
| Linearity of the Product Obtained (% by Weight) | 93.5 |
| Composition of the Product (% by Weight) | |
| 2-Phenylalkane | 50.1 |
| 3-Phenylalkane | 24.6 |
| 4-Phenylalkane | 9.2 |
| 5-Phenylalkane | 4.6 |
| 6-Phenylalkane | 3.7 |
| Didodecylbenzene (% by Weight) | 6.8 |
| Heavy Residue (% by Weight) | 1.2 |

The selectivity of 2-phenylalkane is equal to 50% by weight versus only 28.3% by weight in the case of Example 3. The selectivity of a particular isomer is monitored by the chemical nature of the catalysts that are used.

The operating conditions of the rejuvenation are identical to those implemented in Example 3.

The rejuvenation phase in the reactor 2 lasts for about 24 hours (temperature slope included), then each catalyst in each of the reaction zones of the reactor 2 is left at 120° C. under a stream of benzene until the end of the cycle, in the reactor 1, at the end of which the conversion into olefins is less than 95%. When the conversion into olefins, in the reactor 1, is less than 95%, the functions of each of the reactors 1 and 2 are switched: the reactor 1 passes into the rejuvenation phase, and the reactor 2 passes into the alkylation phase.

After five alkylation/rejuvenation cycles by reactor, the cycle duration during which the conversion of the olefins is greater than 95% decreases. When it becomes equal to 24 hours, a reactivation phase by regeneration of each catalyst in each of the zones (combustion of the coke that is present in each catalyst with an O2/N2 mixture at a temperature that is higher than 450° C.) is then initiated alternately in each of the reactors 1 and 2. When each catalyst of each of the reaction zones of the reactor 2 is regenerated, the reactor 1 operates in alkylation mode, then vice versa.

EXAMPLE 5

Production of Phenylalkanes (According to the Invention)

Two catalytic reactors 1 and 2 are used in parallel, each comprising two reaction zones that contain 25 cm$^3$ of catalyst A in the form of extrudates, prepared according to Example 1.

The reactors 1 and 2 are alternately in alkylation phase and rejuvenation phase.

For the reactor 1, the operating conditions for the alkylation of benzene for each reaction zone are as follows:

Temperature: 120° C.
Pressure: 4 MPa
Benzene/Dodecene-1 molar ratio in each of the reaction zones≈60

A feedstock that contains 86% by weight of benzene and 14% by weight of olefins (C10-C14) is prepared. This feedstock, which is introduced at the inlet of the first reaction zone with a flow rate of 50 cm$^3$/h, contains all of the benzene that is necessary to the alkylation reaction and half the amount of olefins that is necessary to the alkylation reaction. The other half, corresponding to an amount of olefins that is identical to the one that is present in the feedstock that is introduced at the inlet of the first zone, is introduced at the inlet of the second reaction zone by a lateral injection in the middle of the catalytic reactor.

For the reactor 2, the rejuvenation phase is carried out according to the following operating conditions under a flow of benzene:

Temperature: 250° C.
Pressure: 4 MPa
VVH=1.3 h$^{-1}$ (volume of benzene per volume of catalyst and per hour).

The rejuvenation phase lasts for 24 hours, then each of the catalysts of the reaction zones of reactor 2 is passed at 120° C. under a stream of benzene. Then, the reactor 1 passes into a rejuvenation phase after 24 hours of operation with 100% conversion of the olefins and the reactor 2 in alkylation phase according to the operating conditions described above.

After eight alkylation/rejuvenation cycles of 24 hours per reactor, as soon as a drop in conversion of olefins is observed in a 24-hour alkylation cycle (reactor 1 or 2), the reactivation phase by regeneration of each catalyst in a reactor is launched (combustion of the coke that is present in each of the catalysts with an O2/N2 mixture at a temperature of higher than 450° C.) instead of the rejuvenation phase.

TABLE 3

| | |
|---|---|
| Linearity of the Product Obtained (% by Weight) | 92.9 |
| Composition of the Product (% by Weight) | |
| 2-Phenylalkane | 28.2 |
| 3-Phenylalkane | 23.2 |
| 4-Phenylalkane | 19.7 |
| 5-Phenylalkane | 13.3 |
| 6-Phenylalkane | 12.1 |
| Didodecylbenzene (% by Weight) | 2.6 |
| Heavy Residue (% by Weight) | 0.9 |

The invention claimed is:

1. A continuous cyclic process for the production of phenylalkanes that comprises at least:
   a) A reaction for alkylation of at least one aromatic compound by at least one olefin that has 9 to 16 carbon atoms per molecule, whereby said reaction is carried out in at least a first catalytic alkylation reactor within which n serial reaction zones that each contain at least one acidic solid catalyst are present, whereby n is greater than or equal to 2, and at the inlet of each of which one fraction corresponding to 1/n of the total amount of olefins necessary to said alkylation reaction is introduced, and fresh aromatic compound is introduced into the inlet of only the first of said serial reaction zones,
   b) The separation of at least a portion of the effluent that is obtained from stage a) to recover excess reagents, on the one hand, and the phenylalkanes, on the other hand,
   c) The reactivation of each acidic solid catalyst present in each of n reaction zones of at least a second catalytic alkylation reactor placed in parallel relative to said reactor(s) used in said stage a), whereby n is greater than or equal to 2, and
   d) The periodic switching of functions carried out by at least said first catalytic alkylation reactor used in stage a) and at least said second catalytic alkylation reactor that is used in stage c) such that at least said first catalytic alkylation reactor that is initially used in said stage a) is used under the conditions of said stage c) at the end of a duration that is at least equal to 5 hours and such that at least said second catalytic alkylation reactor that is initially used in said stage c) is used under the conditions of said stage a).

2. A process according to claim 1, in which at least said first catalytic alkylation reactor and at least said second catalytic alkylation reactor have the same number n of reaction zones.

3. A process according to claim 1, in which the number of reaction zones in at least each of said first and second catalytic alkylation reactors is less than 10.

4. A process according to claim 1, in which each olefin fraction that is introduced at the inlet of each of said reaction zones is contained in a hydrocarbon-containing feedstock that contains paraffins.

5. A process according to claim 1, in which said olefin has 10 to 14 carbon atoms per molecule.

6. A process according to claim 1, in which said aromatic compound is benzene.

7. A process according to claim 1, in which there is introduced, at the inlet of at least one reaction zone of at least said first catalytic alkylation reactor, an olefin fraction in an amount such that the molar ratio of aromatic compound(s)/olefins is between 21 and 200.

8. A process according to claim 1, in which the olefin fraction that is introduced at the inlet of each of said reaction zones of at least said first catalytic alkylation reactor is such that the molar ratio of aromatic compound(s)/olefins in each of said reaction zones is between 21 and 200.

9. A process according to claim 8, in which the molar ratio of aromatic compound(s)/olefins in each of said reaction zones is between 50 and 100.

10. A process according to claim 1, in which said reactivation according to stage c) is carried out by rejuvenation comprising reactivating each acidic solid catalyst in the presence of at least one aromatic compound.

11. A process according to claim 10, in which said aromatic compound is obtained at least partly from the excess reagents in separation stage b).

12. A process according to claim 10, in which the rejuvenation is carried out at a temperature that is higher than 100° C, under a total pressure that is higher than 1 MPa, with a flow rate of aromatic compound(s) of about 0.01 to 80 volumes per volume of catalyst per hour.

13. A process according to claim 10, in which the rejuvenation is carried out for a duration of between 10 and 50 hours.

14. A process according to claim 1, in which said reactivation according to stage c) is carried out by regeneration that is carried out by combustion of the hydrocarbon-containing radicals that are adsorbed on the active sites of each acidic solid catalyst.

15. A process according to claim 14, in which the regeneration is carried out for a duration of between 20 and 100 hours.

16. A process according to claim 1, in which said reactivation according to stage c) is carried out by rejuvenation and regeneration.

17. A process according to claim 1, in which the same acidic solid catalyst is used in each of the reaction zones of each of said first and second catalytic alkylation reactors.

18. A process according to claim 17, in which said acidic solid catalyst comprises at least one zeolite of the structured type from the group FAU, MOR, MTW, OFF, MAZ, BEA and EUO.

19. A process according to claim 18, in which said zeolite is a FAU-structural-type zeolite.

20. A process according to claim 18, in which said zeolite is a MOR-structural-type zeolite.

21. A process according to claim 18, in which said acidic solid catalyst is a mixture of zeolites.

22. A process according to claim 1, in which the same first acidic solid catalyst is used in each of n reaction zones of said first catalytic alkylation reactor and the same second acidic solid catalyst is used in each of n reaction zones of said second catalytic alkylation reactor.

23. A process according to claim 1, in which at least two reaction zones of said first or said second catalytic alkylation reactor contain a different acidic solid catalyst.

24. A process according to claim 1, further comprising in a process for producing a detergent, reacting a resultant phenylalkane.

* * * * *